(12) United States Patent
Lee et al.

(10) Patent No.: US 7,884,088 B2
(45) Date of Patent: Feb. 8, 2011

(54) FUNCTIONALIZED ORGANIC OLIGOMERS USING HOMOGENEOUS MODIFICATION METHOD FOR MOLECULAR BINDING

(75) Inventors: Dong-Won Lee, Temple Terrace, FL (US); Ronald Howard Baney, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1309 days.

(21) Appl. No.: 11/099,195

(22) Filed: Apr. 5, 2005

(65) Prior Publication Data

US 2005/0249696 A1    Nov. 10, 2005

Related U.S. Application Data

(60) Provisional application No. 60/559,674, filed on Apr. 5, 2004.

(51) Int. Cl.
| | |
|---|---|
| A61K 31/16 | (2006.01) |
| A61K 31/722 | (2006.01) |
| C08B 37/00 | (2006.01) |
| C08B 37/08 | (2006.01) |

(52) U.S. Cl. .......................................... 514/55; 536/20
(58) Field of Classification Search .................. 514/55; 536/20
See application file for complete search history.

(56) References Cited

U.S. PATENT DOCUMENTS

| | | |
|---|---|---|
| 5,721,347 A | 2/1998 | Gross et al. |
| 6,403,675 B1 * | 6/2002 | Dang et al. ................. 523/113 |
| 7,288,532 B1 * | 10/2007 | Payne et al. .................... 514/55 |

FOREIGN PATENT DOCUMENTS

| | | |
|---|---|---|
| DE | 3912122 A1 | 10/1990 |
| EP | 1057529 A1 | 12/2000 |
| EP | 1118623 A1 | 7/2001 |
| WO | WO00/11038 | * 3/2000 |

OTHER PUBLICATIONS

Somorin et al., Studies on Chitin II Preparation of Benzyl and Benxoylchitins, Sep. 22, 1978, Polymer Journal, vol. 11, No. 5, pp. 391-396.*
Quantitative Chemistry: Theoretical and Percent Yield, [online], Retrieved [Feb. 1, 2010], Retrieved from URL:<http://web.archive.org/web/20030112160717/http://www.iun.edu/~cpanhd/C101webnotes/quantchem/thtclandpctyld.html.*

* cited by examiner

Primary Examiner—Frederick Krass
Assistant Examiner—Lezah W Roberts
(74) Attorney, Agent, or Firm—Thomas, Kayden, Horstemeyer & Risley, LLP

(57) ABSTRACT

A method of homogeneously forming functionalized biocompatible oligomers includes the steps of dissolving a biocompatible oligomer in a solvent to form a solution, and admixing at least one π complex forming group to the solution, wherein the π complex forming group grafts to at least one location on the backbone of the oligomer to form a grafted oligomer. The oligomer is preferably oligochitosan and the solvent is preferably dimethylsulfoxide (DMSO). The degree of graft substitution can be at least 50%. The functionalized biocompatible oligomer can be used for drug detoxification through binding to a variety of target drugs.

16 Claims, 7 Drawing Sheets a) Amitriptyline b) Oligochitosan (n=3-5)

c) Benzenesulfonyl chitosan d) Dinitrobenzenesulfonyl chitosan

FUNCTIONALIZED ORGANIC OLIGOMERS USING HOMOGENEOUS MODIFICATION METHOD FOR MOLECULAR BINDING

CROSS-REFERENCE TO RELATED APPLICATIONS

This application claims the benefit of Provisional Patent Application No. 60/559,674 entitled "FUNCTIONALIZED ORGANIC OLIGOMERS USING HOMOGENEOUS MODIFICATION METHOD" filed on Apr. 5, 2004, which is hereby incorporated by reference into the present application in its entirety.

STATEMENT REGARDING FEDERALLY SPONSORED RESEARCH OR DEVELOPMENT

The United States Government has rights in this invention pursuant to National Science Foundation (NSF) Grant No. EEC-94-02989.

FIELD OF THE INVENTION

The invention relates to functionalized organic oligomer particles and homogeneous modification methods for forming the same.

BACKGROUND OF THE INVENTION

Chitosan is a linear copolymer of N-acetyl-D-glucosamine and D-glucosamine linked by glucosidic linkage. Chitosan may be derived from chitin, which is the second most abundant natural polymer. Chitosan is formed through N-deacylation of the chitin molecule. Chitin is found in the exoskeleton of shellfish such as shrimp, lobster, and or crabs. Chitin may also be found in the exoskeleton of insects.

Chitosan may also be used as a precursor for value-added polymers in biomedical and pharmaceutical areas due to the non-toxic aspect of chitosan. Chitosan has also shown some biologic activity, as well as biocompatibility, biodegradability, and/or potential of physical and chemical modification.

Some attention has been placed on the modification reaction of chitosans to construct sophisticated molecular architecture having various advanced functions. High molecular weight chitosans, generally averaging at least 10,000 Daltons, have been prepared as functionalized nanoparticles and have been reported to have pharmaceutical and medical applications. However, chitosan is generally very difficult to modify chemically due to the strong inter and intra molecular hydrogen bonding. As a result, high molecular weight chitosan has been modified under heterogeneous conditions due to the poor solubility of chitosan in organic solvents, generally leading to a low degree of substitution and low yield of functionalized chitosan products.

SUMMARY

A method of homogeneously forming biocompatible oligomer derivatives includes the steps of dissolving a biocompatible oligomer in a solvent to form a solution, and admixing at least one π complex forming group to the solution, wherein the π complex forming group grafts to at least one location on the backbone of the oligomer to form a grafted oligomer.

The solvent can comprise dimethylsulfoxide (DMSO), gamma butyrolactone (GBL), propylene carbonate, N-methylpyrrolidinone (NMP), tetrahydrothiophen-1, 1-dioxide (TMS), polycarbonate (PC), methyl isobutyl ketone or dimethyl formamide (DMF). The π complex forming group grafted can be benzenesulfonyl, dinitrobenzenesulfonyl, benzoyl, dinitrobenzoyl or naphthoyl. The oligomer is preferably a natural oligomer, being oligochitin and oligochitosan. In a preferred embodiment, the biocompatible oligomer comprises oligochitosan having an average molecular weight of less than 3,000 Da.

The degree of substitution of the grafts is preferably at least 20%, such as at least 40%. The method can provide a yield of grafted oligomer of at least 40%. The grafted oligomer is generally water soluble.

A π-complex forming group functionalized biocompatible oligomer comprises an oligomer grafted with at least one π complex forming group. The oligomer is preferably oligochitin or oligochitosan. The oligochitosan or oligochitin preferably has an average molecular weight of less than 6,000 Da, such as less than 3,000 Da. The degree of substitution of the complex forming group can be at least 20%.

A method of drug detoxification comprises the step of providing a π-complex forming group functionalized biocompatible oligomer. The oligomer is grafted with at least one π complex forming group. The functionalized biocompatible oligomer is introduced into a body of a subject, wherein the functionalized biocompatible oligomer binds to at least one target drug in the body of the subject. The target drug can be an antidepressant, such as amitriptyline, imipramine, desipramine, Maprotiline or protriptyline.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION

Figure 1:
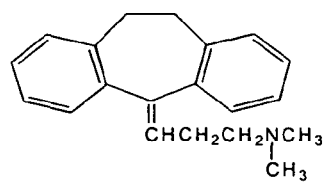
FIGS. 1(a), (b), (c) and (d) show the chemical structure of amitriptyline, oligochitosan, and one repeat unit of benzenesulfonyl substituted chitosan and dinitrobenzenesulfonyl substituted chitosan according to the invention, respectively.
Figure 1:
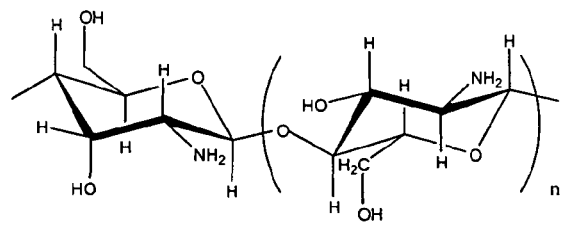
Figure 1:
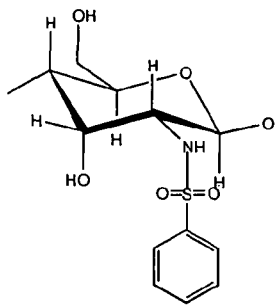
Figure 1:
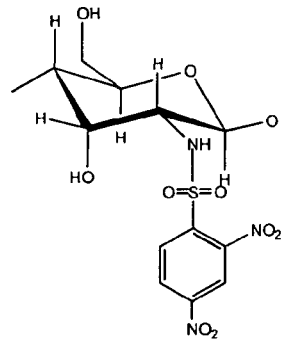

The invention describes a homogenous chemical reaction to graft functionalities onto oligomers such as oligochitosan to prepare previously unobtainable oligomer derivatives with well-defined structure for advanced applications. The oligomer is preferably highly blood-compatible, non-toxic, biologically active, biocompatible, biodegradable and is capable of being functionalized with a π-complex forming group. Generally, preferred oligomers for use with the invention include the amine functionality. For example, the oligomer can comprise oligochitosan, as well as its derivatives. Thus, although the invention is described with respect to oligochitosan, the invention can also be generally applied to other oligomers including oligochitin.

Even though chitosan is commercially available, oligochitosan is not generally commercially available and has not drawn much attention in the literature. Oligochitosan may be prepared by cleaving of chitosan chains to form a material having an average degree of polymerization (DP) of less than 20, preferably being less than about 10. Oligochitosan may be formed by cleaving chitosan using methods including acidic hydrolysis, enzymatic degradation and irradiation. Oligochitosan has been shown to be more biocompatible and biodegradable than chitosan.

As used herein, the term "oligomer" refers to a repeat unit comprising molecule having a degree of polymerization of from about 2 to about an average of 20. Accordingly, for the present invention, low-molecular weight chitosan refers to a chitosan sample having an average molecular weight generally equal to or less than about 6,000 Da. In alternative embodiments, the oligochitosan has an average molecular weight of less than about 5,000, less than about 4,000 or less than about 3,000 Da. In yet other embodiments, the oligochitosan has an average molecular weight of less than about 1,500 Da. For drug scavenging applications, lower molecular weight oligomers are generally preferred due to their improved blood compatibility compared to their higher molecular weight counterparts. Alternatively, the oligomers according to the invention can include repeat unit structures having an average molecular weight low enough to be soluble in a solvent, such as DMSO.

Chitosan and chitin lack functionality to bind to hydrophobic molecules, such as tricyclic amitriptyline. Thus, to provide binding ability to these molecules, oligomers such as oligochitosan are chemically modified to add functional groups which impart selective binding ability. One possible route for selective binding adds one or more aromatic π complex forming groups to the backbone of the oligomer. It is believed that π complex forming groups once chemically bound to chitosans or chitins according to the invention not only selectively bind drugs such as amitriptyline by aromatic-aromatic interactions, but also deactivate the toxicity of the target drug once selectively bound.

Drug detoxification is the antithesis of drug delivery. Tricyclic antidepressant amitriptyline was chosen as a target drug to evaluate the efficacy of substituted oligochitosans according to the invention because it was the most widely prescribed antidepressant at the time of the invention and is known to be used for committing suicide.

FIG. 1(a) shows the chemical structure of amitriptyline, which is one of the drugs which may be targeted by grafted oligomers according to the invention. Amitriptyline is a tricyclic aromatic comprising molecule which belongs to the first generation of antidepressant drugs and is reported to be extremely hydrophobic and cardiotoxic. Although the invention is described herein for the treatment of drug overdoses due to amitriptyline, the invention can be used to target other drugs, such as imipramine, desipramine and protriptyline which are also tricyclic antidepressants belonging to the first generation of antidepressant drugs, as well as Maprotiline which is tricyclic and belongs to second generation antidepressants.

FIG. 1(b) shows two repeat units of oligochitosan, while FIGS. 1(c) and (d) show one repeat unit of benzenesulfonyl chitosan and dinitroberizenesulfonyl chitosan, respectively. The benzenesulfonyl and dinitrobenzenesulfonyl groups bound to the chitosan monomers shown in FIGS. 1(c) and (d), respectively, are π-complex forming group. The resulting substituted oligochitosans have been found to remain highly soluble in neutral water after chemical modification according to the invention.

Although not needed to practice the claimed invention, Applicants, not seeking to be bound to theory, present the following mechanism for the binding of drugs to substituted biopolymers including substituted chitosans according to the invention. In the presence of substituted chitosans, such as benzenesulfonyl chitosan and dinitrobenzenesulfonyl chitosan, amitriptyline appears to become bound to the substituted chitosans via π-π complex formation.

One of the strongly desired characteristics for drug detoxification is the selective binding toward target drugs. Hydrophilic chitosan does not have a selective binding capability for tricyclic hydrophobic amitriptyline. Functionalized oligochitosans able to selectively bind amitriptyline can be obtained through the chemical modification according to the invention. Chemical modification of chitosan has been studied for various purposes, such as enhancement of solubility in water or organic solvents, introduction of hydrophobicity, and development of blood compatibility and stealth properties. However, the reported modification reactions have been performed with high molecular weight chitosans generally having a molecular weight of tens of thousands of Da under heterogeneous conditions due to the poor solubility of the high molecular weight chitosan in organic solvents.

The invention provides methods for homogeneous chemical modification of oligomers, such as oligochitosan, with π-π complex forming groups. Selective binding toward amitriptyline is based on the assumption that electron deficient aromatic rings chemically bound to oligochitosan not only selectively bind the amitriptyline but also deactivate its toxicity. Aromatic-aromatic interaction is commonly observed in biological molecules such as DNA, drugs and protein and molecular recognition. Although the magnitude of this attractive interaction is relatively small (2 to 5 kcal/mol), the interaction is believed to play an essential role in natural self-assemblies and molecular recognition processes.

Intravenously injectable functionalized oligochitosan derivatives capable of selectively reducing the free concentration of drugs including toxic amitriptyline in the bloodstream can be synthesized under homogeneous conditions to have a high degree of aromatic ring substitution as follows. Oligochitosan is first obtained, such as through enzymatic degradation of commercially available chitosan. Before the reaction, the oligochitosan is preferably dried in a vacuum.

Oligochitosan powder has been found to readily dissolve in dimethylsulfoxide $(CH_3)_2SO$ (hereafter DMSO). DMSO is believed to efficiently break up hydrogen bonding in the oligomer sample, but not participate in the chemical modification processes described herein. Accordingly, preferred solvents for use with the invention provide a sufficient hydrogen bond basicity to permit solubility of the oligomer of interest therein. Solvents other than DMSO which generally have sufficient hydrogen bond basicity capable of dissolving oligomer powders and not participating in the chemical modification processes described herein may include gamma butyrolactone (GBL), propylene carbonate, N-methylpyrrolidinone (NMP), tetrahydrothiophen-1,1-dioxide (TMS), polycarbonate (PC), methyl isobutyl ketone and dimethyl formamide (DMF).

The oligochitosan is preferably dissolved in DMSO along with a reagent for providing grafts to the chitosan. For example, dinitrobenzenesulfonyl chloride or benzenesulfonyl chloride can be used for this purpose. The reaction mixture is generally stirred and can be left for several days. The resulting modified oligochitosan product formed can be precipitated by adding ethanol, and subsequently separated by centrifugation. The final product can be soxhlet-extracted with methanol overnight, and dried in a vacuum.

Several aromatic functional groups such as benzenesulfonyl, dinitrobenzenesulfonyl, benzoyl and dinitrophenyl groups, were successfully grafted to the chitosan backbone with high degree of substitution in DMSO, which was confirmed by a spectroscopy as described below. This process provides not only a high yield of products (>60%) but also a high degree of substitution, such as al least 20%, 30%, 40%, and preferably and at least 50%. The product yield can be further improved by improvements in the precipitation percentage of the product as well as filtering methodology. The degree of substitution relates to the percentage of monomers which include grafts. Thus, a 50% degree of substitution for a 12 monomer oligomer would include grafts on 6 of the 12 monomer units. Higher drug efficacy generally results from oligomers having higher degrees of substitution.

Prepared oligochitosan derivatives according to the invention are soluble in even neutral water, and have also been found to be blood compatible. Water solubility and blood compatibility of oligochitosan derivatives eliminate the process of nanoparticle formation. One of the potential applications for these particles is the drug detoxification. Oligochitosan derivatives can be injected into the blood stream to bind selectively hydrophobic toxic drugs with electron sufficient aromatic rings (e.g., trycyclic antidepressant, amitriptyline). NMR data has demonstrated that modified oligochitosans according to the invention bind the drugs. Isolated heart tests have revealed that modified oligochitosan significantly attenuate amitriptyline-induced cardiac toxicity.

A method of treating drug overdoses includes the steps of providing a π-complex forming group functionalized biocompatible oligomer, and intravenously administering the functionalized oligomer to a drug intoxicated subject. As a result, the functionalized oligomer binds to a target drug in the bloodstream, such as via a π-π complexation mechanism. Once bound, the toxicity of the target drug is eliminated, or at least substantially reduced.

A pi-complex is also known in the art as an adduct. A pi-complex or adduct refers to a new chemical species, e.g. AB, each molecular entity of which is formed by direct combination of two separate molecular entities A and B in such a way that there is change in connectivity, but no loss, of atoms within the respective moieties A and B. Stoichiometries other than 1:1 are also possible, e.g. a bis-adduct (2:1). An adduct or pi-complex is formed by electron-pair donation from a pi orbital into a sigma orbital, or from a sigma orbital into a pi orbital, or from a pi orbital into a pi orbital. For example:

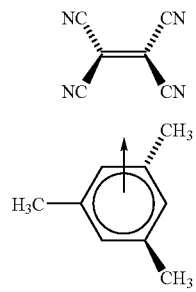

Hereafter, such a combination will be referred to as a "pi complex", while a species such as trimethyl benzene shown above, is referred to herein as a π-complex forming group.

Although unmodified biocompatible biopolymers or oligomers, such as chitosans have been prepared as nanoparticles for oral and nasal administration, no known research has been identified regarding the intravenous administration of functionalized biocompatible polymer or oligomer systems, such as π-complex forming functionalized biocompatible biopolymers or oligomers, including functionalized chitosan-based system.

The π-complex forming group is generally an aromatic molecule having at least one aromatic ring which is capable of being bound to biopolymers or oligomers according to the invention as well as forming a π-complex with a desired target drug. For example, benzenesulfonyl, dinitrobenzenesulfonyl, dinitrophenyl, benzoyl, dinitrobenzoyl and naphthoyl groups can be used, such as with oligomers according to the invention for binding to amitriptyline and related drugs. However, conjugated molecules, such as 1,3 butadiene, which have π electrons which interact to form a continuous π cloud (resonance) are also π-complex forming groups which may be used with the invention.

The particular π-complex forming group selected is preferably based on the strength of the resulting π-complex with a particular desired target drug. Thus, the preference for particular π-complex forming groups generally depends on the π-electron density of aromatic rings on target drug. For example, for amitriptyline adsorptions the dinitrobenzenesulfonyl group is generally preferred, followed by dinitrophenyl group and then the benzenesulfonyl group.

Noncovalent interaction between aromatic moieties is observed in binding of biological molecules such as DNA, certain drugs and certain proteins. Although the magnitude of this attractive interaction is relatively small (2~5 kcal/mol), the interaction is believed to play an essential role in many natural self-assemblies and molecular recognition processes. A number of studies have been conducted to assess the structural, geometrical and energetic parameters of this noncovalent interaction. It has been suggested that the aromatic-aromatic interaction is driven mainly by electrostatic and dispersion forces.

The invention is expected to have a broad range of applications. Although described herein relative to drug detoxification, the invention can also be used for other applications, such as drug delivery. In the case of drug delivery, functionalized polymer or oligomer particles having a given drug bound thereto can be administered to a patient. The drug is then controllably released from the functionalized particle.

Chitosan is known to adsorb heavy metals, mercury, lead, nickel and chromium by complexation, chelation, or ion exchange. Thus, the invention has applications beyond biological systems. For example, functionalized oligochitosan and oligochitin according to the invention can be used for environmental remediation, such as for removal of heavy metals. The invention can be used for removal of pesticides and insecticides.

Modified oligochitosans and oligochitins according to the invention are expected to also be useful for the nuclear industry. For example, modified oligochitosans and oligochitins according to the invention can be used to adsorb actinide in nuclear waste water and, thus, separate actinides from lanthanides.

EXAMPLES

The present invention is further illustrated by the following specific examples, which should not be construed as limiting the scope or content of the invention in any way.

Oligochitosan prepared by enzymatic degradation was obtained from E-ZE Co. LTD (Korea) and used without further purification. The average molecular weight and moisture, as determined by the supplier, were 1,150 Da, and 8.0%, respectively. Dinitrobenzenesulfonyl chloride, benzenesulfonyl chloride and amitriptyline were purchased from Aldrich and used as received.

Before the reaction, the chitosans were dried in a vacuum. Three grams of oligochitosan powder were dissolved in DMSO (15 mL) containing dinitrobenzenesulfonyl chloride (2.5 g) or benzenesulfonyl chloride (3.3 g). The reaction mixture was stirred and left for two days at room temperature. The resulting modified oligochitosan product was precipitated by adding ethanol, and subsequently separated by centrifugation. The final product was soxhlet-extracted with methanol overnight, and dried in a vacuum.

Figure 2A:
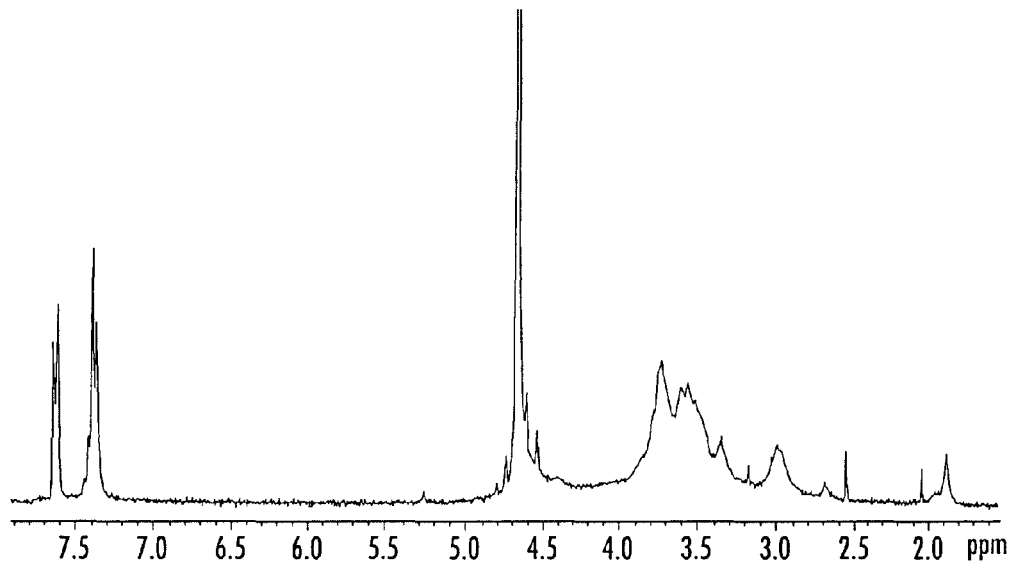
FIGS. 2(a) and (b) show H-NMR results obtained from benzenesulfonyl chitosan and dinitrobenzenesulfonyl chitosan, respectively.
Figure 2B:
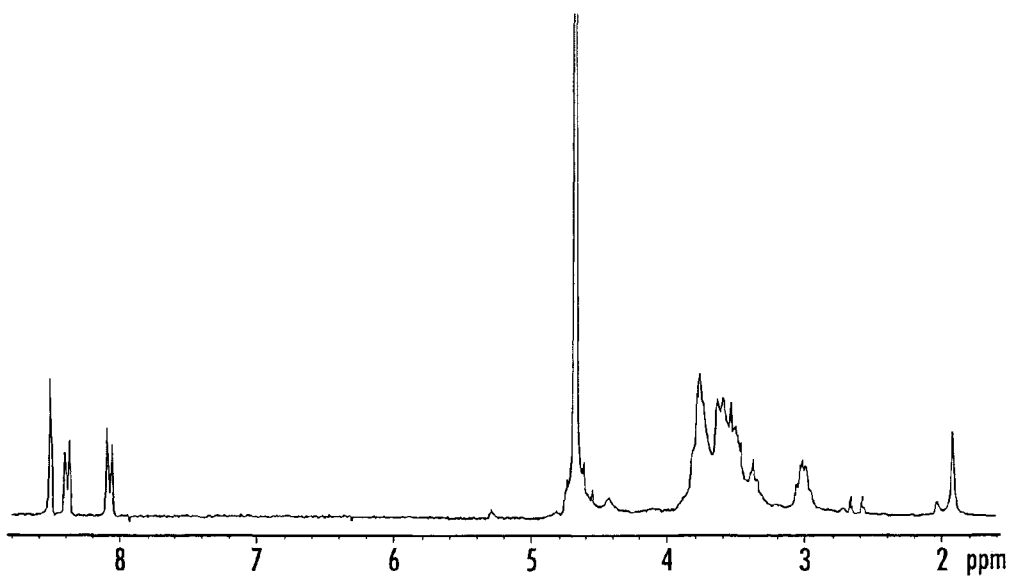

FIGS. 2(a) and (b) show $^1$H-NMR spectra of the oligochitosan derivatives benzenesulfonyl and dinitrobenzensulfonyl, respectively, which were obtained with a Varian VXR 300 (300 MHz) using $D_2O$ as a solvent. Chemical shifts were referenced to the internal water signal at 4.67 ppm. The signal at 1.7 corresponds to the acetyl protons of N-acetylglucosamine units. The protons at carbons (C-2) bearing amino groups are assigned to the signal at 2.8 ppm. The degree of deacetylation of the oligochitosan was calculated to be 65% from the integral intensity between protons on C-2 and acetyl protons of N-acetyl-glucosamine.

Further detailed assignment of all resonance signals was not attempted. However, one important feature of these spectra is the appearance of new signals above 7 ppm. This region is typical for aromatic proton resonance. Benzenesulfonyl chitosan shows two signals with a clear distinction (gap) at 7.4 and 7.6 ppm, corresponding to meta and para protons and ortho protons, respectively. The ortho protons are more deshielded than meta and para protons because of the magnetic anisotropy of the π bonds in the aromatic ring. The ratio of integral intensity of meta and para protons to ortho protons is 1.5:1. Dinitrobenzenesulfonyl oligochitosan shows three signals above 8 ppm with the identical integral intensity. The degree of substitution of oligochitosan was calculated to be around 40% from the integral ratio between aromatic protons and protons at carbons (C-2).

Figure 3:
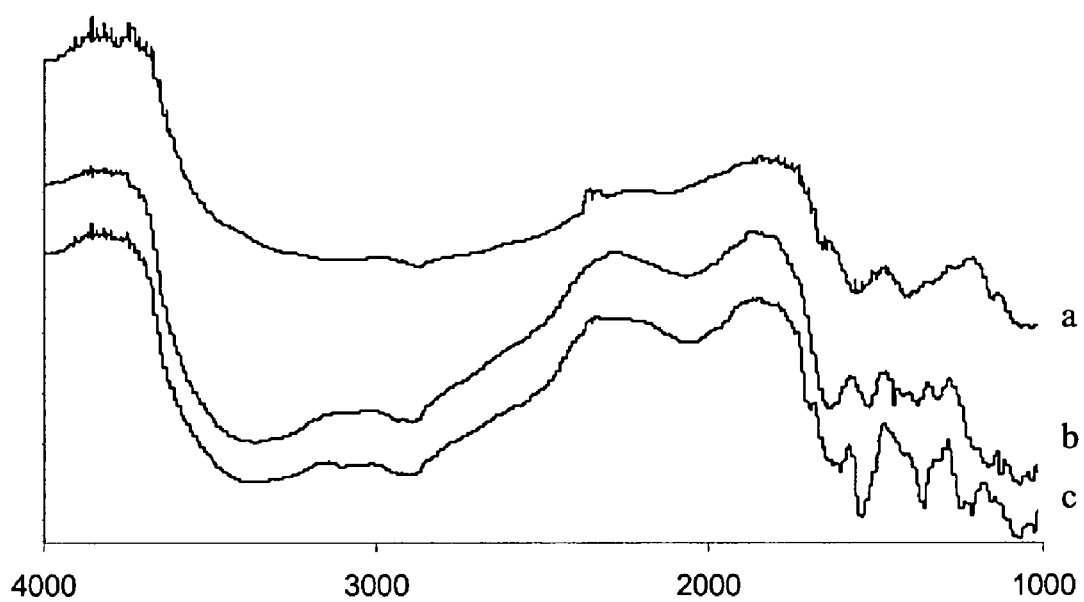
FIGS. 3(a)-(c) show FT-IR data derived from unmodified chitosan, and the chitosan functionalized derivatives benzenesulfonyl chitosan and dinitrobenzenesulfonyl chitosan according to the invention, respectively.

FIG. 3(a)-(c) show FT-IR data derived from unmodified chitosan, and the chitosan functionalized derivatives benzenesulfonyl chitosan and dinitrobenzenesulfonyl chitosan according to the invention, respectively. The analysis was performed using an FT-IR (Nicolet Magna, USA) with a KBr drift method. The strong bands at approximately 1550 $cm^{-1}$ and 1600 $cm^{-1}$ are attributed to the amide groups. The very strong band at 1550 $cm^{-1}$ of dinitrobenzenesulfonyl oligochitosan is attributed to the asymmetric stretch of aromatic nitro groups. Asymmetric stretch of S=O in sulfonamide groups is represented at 1325 $cm^{-1}$. The spectroscopic results clearly demonstrate that benzenesulfonyl and dinitrobenzenesulfonyl groups are successfully grafted to the oligochitosan backbone.

Figure 4:
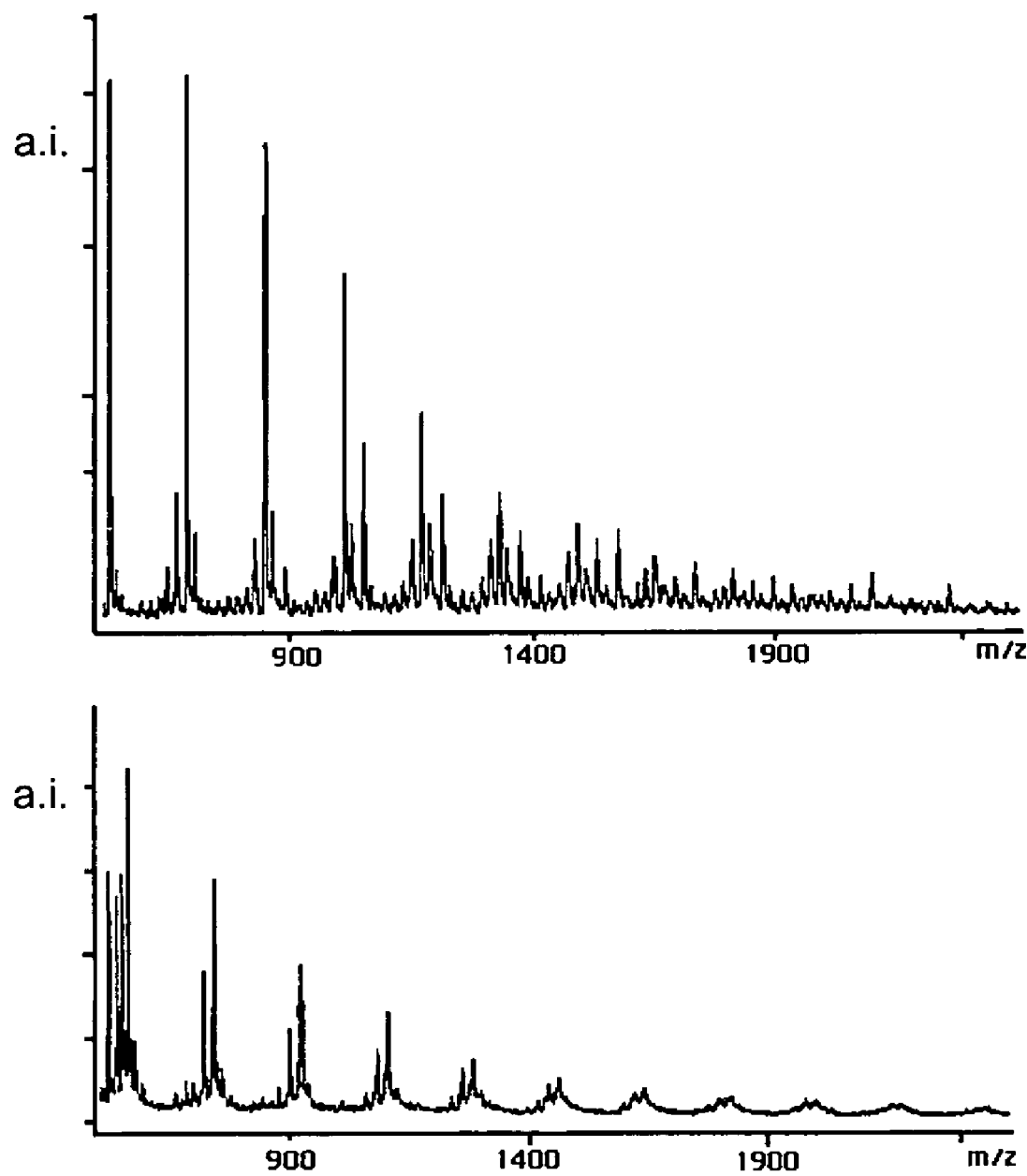
FIGS. 4(a) and (b) provide MALDI-TOF spectra for pure chitosan and benzenesulfonyl chitosan, respectively.

FIGS. 4(a) and (b) show MALDI-TOF spectra for molecular weight determinations of pure chitosan and benzenesulfonyl chitosan, respectively. For the MALDI-TOF analysis, chitosan was dissolved in $H_2O$ to which dihydroxylbenzoic acid was added as a matrix. The ratio of matrix to analyte is 100:1.

MALDI-TOF has been used to investigate the biological molecules such as protein and enzyme and analyze the endgroups and repeating units of polymers up to 30,000 Da. Unmodified oligochitosan shows a broad molecular weight distribution (dp of 3 to about 7). However, it is clear that the difference of the adjacent two major peaks is 161. This corresponds to the molecular weight of one D-glucosamine monomer unit, although chitosan consists of N-acetyl-D-glucosamine and D-glucosamine. It seems likely that benzenesulfonyl oligochitosan shows a similar pattern of molecular weight distribution. However, not only the molecular weight but also the discrepancy between adjacent two major peaks increased after the chemical modification may be to the attachment of functional groups to oligochitosan molecules.

Thromboelastography was investigated using substituted oligichitosans according to the invention. Thromboelastography (TEG) measures the viscoelastic properties of blood as it is induced to clot under a low shear environment similar to sluggish blood flow in the body. TEG characterizes the formation and strength of the blood clot as a function of time.

Whole blood was obtained from 3 healthy male adults (24-31 year old). Thromboelastography (TEG) was carried out using a Thromboelastograph Coagulation Analyzer (Model 3000C, Haemoscope, Co. Skokie, Ill., USA). Each oligochitosan in saline solution (30 μL) was pipetted into TEG™ cuvettes prewarmed to 37° C. A $CaCl_2$ solution of 30 μL and whole blood of 240 μL were added into the cuvettes. The same volume of saline solution was used as a control. The pins of TEG™ were partially raised and lowered three or four times in order to ensure uniform mixing of the blood with the samples and standardize the agitation/activation of all blood specimens. Mineral oil was placed on the surface of the specimen to prevent air from drying out the samples. The TEG profile was obtained on a chart running at 2 mm/min.

Figure 5:
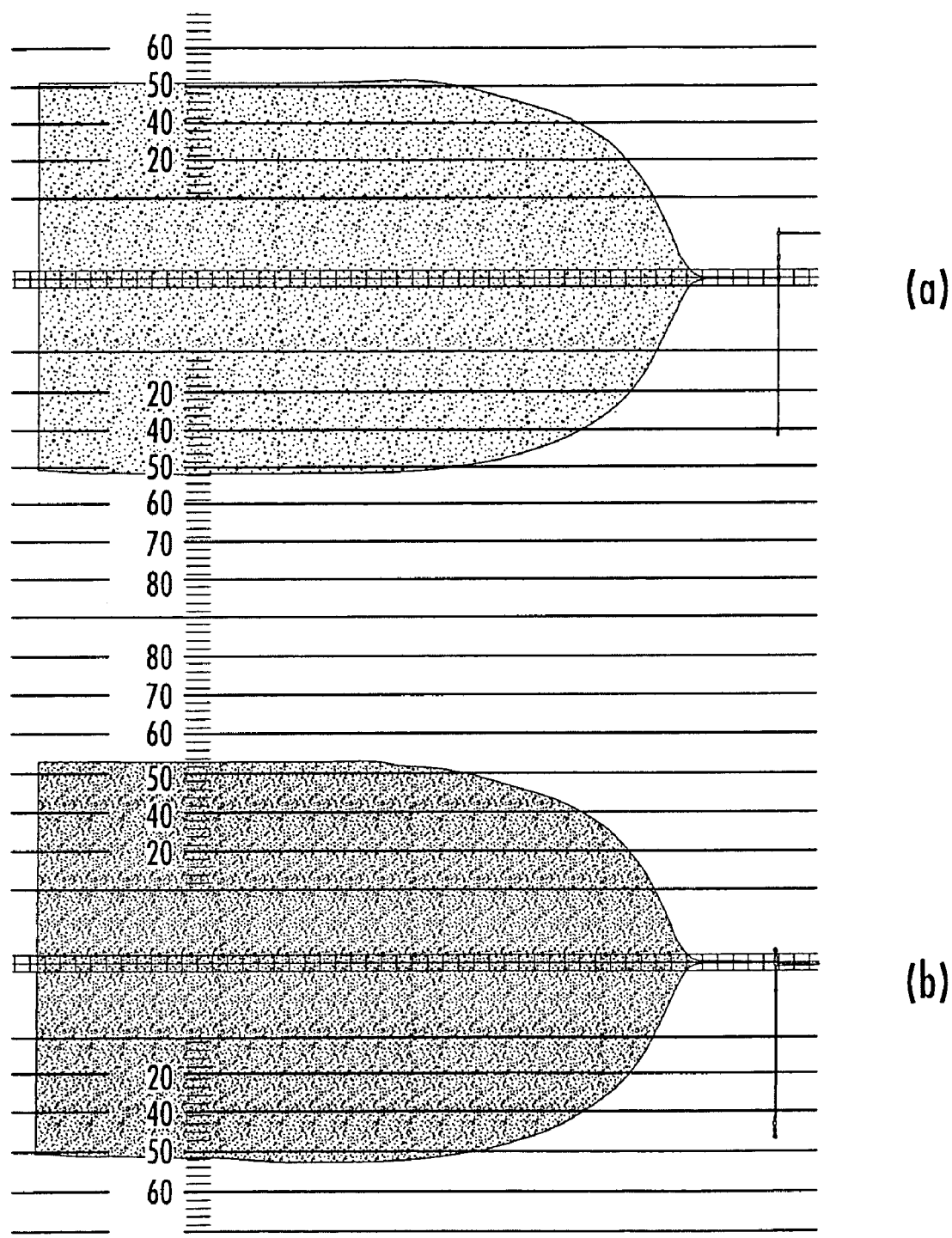
FIGS. 5(a) and (b) provide TEG tracings of blood with a saline solution and dinitrobenzenesulfonyl chitosan, respectively.

Formation of a clot is graphically represented as a characteristic cigar shape profile over time. TEG tracing profiles have some principle parameters to be considered. Reaction time, R, is the period of time from initiation of the test to the initial fibrin formation. K is a measure of time from beginning of clot formation until the amplitude of thromboelastogram reaches 20 mm and represents the dynamics of clot formation. An α angle is an angle between the line in the middle of the TEG tracing and the line tangential to the TEG curve. Maximum amplitude (MA) is the maximum amplitude of the tracing and represents the strength of a clot. FIGS. 5(a) and (b) represent TEG profiles of blood with saline solution and an oligochitosan solution according to the invention, respectively. Saline solution was used as a negative control. No significant change was observed in the apparent shape, illustrating that unmodified, benzenesulfonyl and dinitrobenzenesulfonyl oligochitosan are compatible with blood. TEG data from different functional groups were compared by the "Two Way Repeated Measures ANOVA". A p-value less than 0.05 was considered significant. There was no significant difference between oligochitosan-treated groups and saline solution-treated control. In addition, no significant difference was observed between pure chitosan and modified oligochitosans at the concentration of 1.0 and 0.1% in a saline solution. It is noted that a preliminary experiment showed that benzenesulfonyl and dinitrobenzenesulfonyl chitosan did not manifest acute cardiotoxicity and weight gain or loss for 4 weeks, when intravenously administrated into a rat.

As shown in FIG. 1 (a), amitriptyline has two aromatic rings with high relative π-electron density because of the neighboring π electron in the double bond and the electron donating nature of methylene groups. Benzenesulfonyl and dinitrobenzenesulfonyl groups have less π electron density compared to unsubstituted benzene rings because the sulfone and nitro groups are electron withdrawing. These electron rich and electron poor aromatic rings form π-π complexes (or donor-acceptor complexes).

Various experimental methods have been adapted to examine π-π complexes including $^1$H-NMR which has been successfully used to examine the aromatic-aromatic interaction because it is extremely sensitive to small changes in the electronic environment of a magnetic nucleus. In addition, it is experimentally easier to measure a peak position than an intensity in the spectrum. In $^1$H-NMR, π-π complexation through the aromatic-aromatic interaction is observed by monitoring the chemical shift of a given aromatic proton. Generally, chemical shift of protons on electron deficient (accepting) aromatic rings is monitored when electron rich (donating) aromatic rings are present in excess.

Figure 6A:
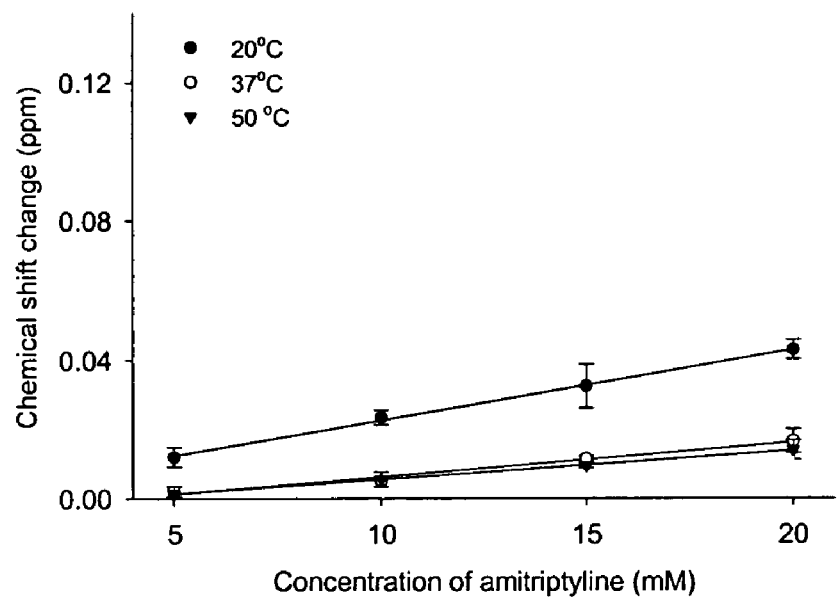
FIGS. 6(a) and (b) show the variation in chemical shift of aromatic protons for benzenesulfonyl oligochitosan and dinitrobenzenesulfonyl oligochitosan, respectively.

A $^1$H-NMR experiment for monitoring aromatic-aromatic interaction was carried out in $D_2O$ at 20, 37 and 50° C. Stock solutions of oligochitosan and amitriptyline were prepared in $D_2O$ at the concentration of 10 mM and 40 mM, respectively. Two stock solutions were mixed to give a various ratio of oligochitosan to amitriptyline with a fixed concentration of chitosan, 5 mM. The ratio of oligochitosan to amitriptyline was varied from 1:1 to 1:4. FIGS. 6(a) and (b) show the variation in chemical shift of aromatic protons in benzenesulfonyl oligochitosan and dinitrobenzenesulfonyl oligochitosan, respectively. The oligochitosan concentration was 5 mM and the concentration of amitriptyline was varied from 5 to 20 mM. The signal corresponding to meta and para protons of benzenesulfonyl groups was utilized to monitor the aromatic-aromatic interaction. Benzenesulfonyl aromatic protons were shifted upfield upon the addition of amitriptyline.

The upfield shift of electron deficient aromatic protons can be explained by the magnetic anisotropy associated with an increased ring current shielding of electron rich aromatic rings. When electron deficient benzenesulfonyl rings form complexes with electron rich amitriptyline aromatic rings in a favored complexation geometry, benzenesulfonyl protons are more shielded by increased number of π electrons.

A clear increase in the chemical shift variation is observed with increasing amitriptyline concentration, suggesting that as the concentration of electron rich aromatic rings increases, more benzenesulfonyl groups participate in the π-π complexation. Ortho protons have the similar manner in chemical shift and the same magnitude of chemical shift variation. The largest variation observed was relatively low, 0.04 ppm (12 Hz), compared to the previously reported intermolecular π-π interaction. Some solute-solute complexes (mixed association) and self-association by π-π interactions or van der Waals force were reported to have the variation in the chemical shift ranging from 25 to 250 Hz for $^1$H-NMR. The small change in observed chemical shift mat be attributed to the high mobility of the counterpart aromatic rings with a slight preference for the complexation geometry. It appears that benzenesulfonyl groups have the temperature dependent aromatic-aromatic interaction. Notable is that the largest variation of chemical shift is observed at the lowest temperature, 20° C. This result can be rationalized by dissociation taking place at the high temperature because of increased molecular kinetic energy which is unfavorable for association. It also seems likely that this aromatic-aromatic interaction is not strong enough to outweigh the reduced entropy caused by association at 37 and 50° C.

Figure 6B:
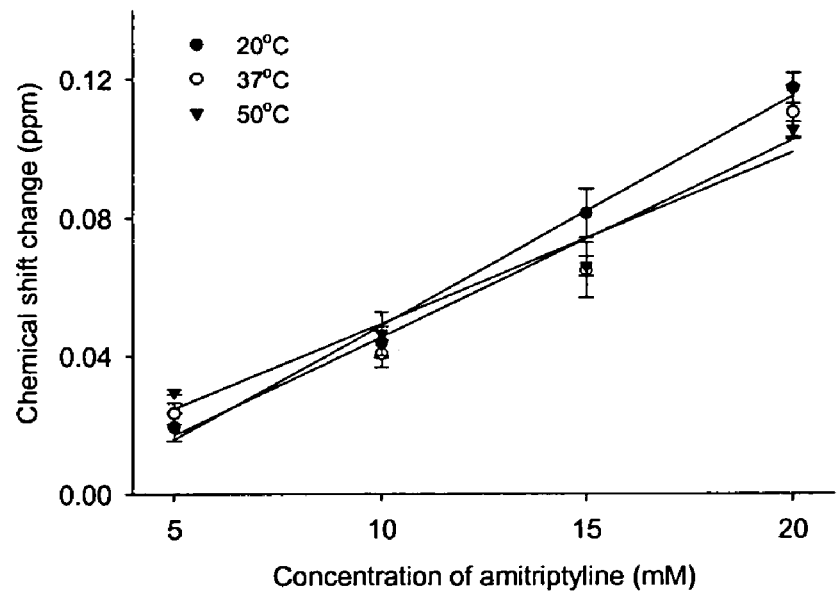

As shown in FIG. 6(b), dinitrobenzenesulfonyl oligochitosan shows similar upfield behavior in the chemical shift change as compared to the benzenesulfonyl chitosan shown in FIG. 6(a). The increased concentration of electron rich aromatic rings is believed to lead to the increased chemical shift variation seen. All three different protons have the identical magnitude of chemical shift variation. However, dinitrobenzenesulfonyl protons have a larger variation than benzenesulfonyl protons at the same concentration of amitriptyline. This effect is primarily due to the strong electron-withdrawing nitro groups which results in the stronger aromatic-aromatic interaction. The presence of electron-withdrawing nitro groups decreases the π electron density around the aromatic ring, consequently, enhancing complexation through π electron donor-acceptor interactions.

It has been also suggested that the closeness between aromatic rings is enhanced by the charge-induced dipole interactions. Based on this rationale, dinitrobenzenesulfonyl groups are supposed to form a π-π complex with a shorter distance between aromatic rings. In contrast to benzenesulfonyl oligochitosan, dinitrobenzenesulfonyl oligochitosan show no temperature dependence in the aromatic-aromatic interaction. The magnitude of chemical shift variation was not influenced by temperature. To examine the dissociation of this π-π complex temperature was increased up to 80° C. However, no temperature effect was observed in the variation of chemical shift. A reasonable explanation for this result involves consideration of association strength and molecular kinetic energy. As mentioned earlier, dinitrobenzenesulfonyl groups form the strong π-π complex thorough the complementary electrostatic interaction between electron deficient and electron rich aromatic rings. The magnitude of complementary electrostatic interaction may be large enough to overcome the increased molecular kinetic energy which can cause them to dissociate at high temperatures.

Figure 7A:
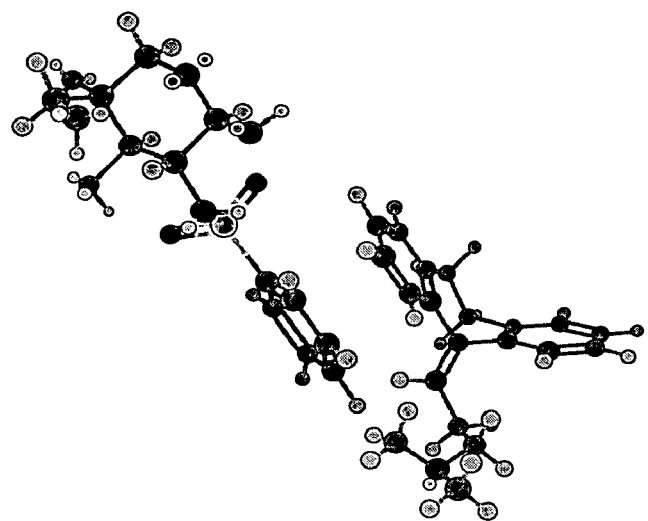
FIGS. 7(a) and (b) show possible models for π-π stacking of benzenesulfonyl and dinitrobenzenesulfonyl chitosans with amitriptyline, respectively.
Figure 7B:
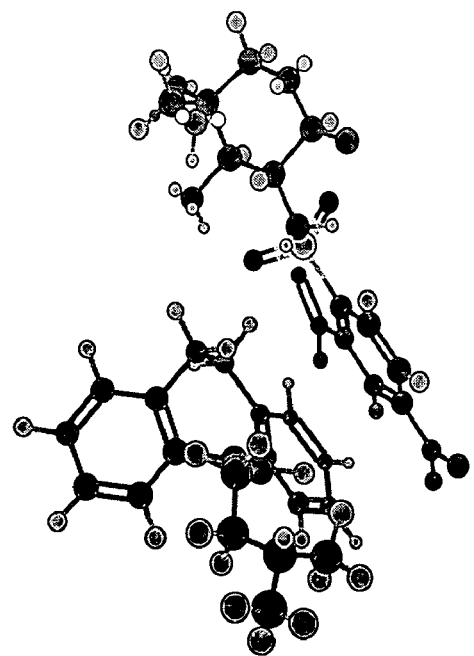

Aromatic-aromatic interactions have several different conformations (geometry) because the interactions are resulted from different factors including electrostatic, hydrophobic and van der Waals interaction. Benzene rings and substituted aromatic regions have been reported to form an aromatic stacking complex which is held together by electrostatic interactions of the π electron system. This suggests that the structures shown in FIG. 7(a) and (b) as possible models for π-π stacking of benzenesulfonyl and dinitrobenzenesulfonyl chitosans with amitriptyline, respectively.

It should be understood that the examples and embodiments described herein are for illustrative purposes only and that various modifications or changes in light thereof will be suggested to persons skilled in the art and are to be included within the spirit and purview of this application, such as the use of alternative cues. The invention can take other specific forms without departing from the spirit or essential attributes thereof.

We claim:

1. A method of homogeneously forming biocompatible oligomer derivatives, comprising the steps of:
    dissolving a biocompatible oligomer selected from the group consisting of oligochitin, oligochitosan, and derivatives thereof in a solvent to form a solution, and
    admixing at least one π complex forming group into said solution,
    wherein a grafted oligomer is formed, said grafted oligomer comprising at least one of said π complex forming groups grafted to a backbone of said oligomer, and
    wherein said grafted oligomer is soluble in neutral water.

2. The method of claim 1, wherein said solvent comprises dimethylsulfoxide (DMSO).

3. The method of claim 1, wherein said solvent comprises at least one selected from the group consisting of gamma butyrolactone (GBL), propylene carbonate, N-methylpyrrolidinone (NMP), tetrahydrothiophen-1, 1-dioxide (TMS), polycarbonate (PC), methyl isobutyl ketone and dimethyl formamide (DMF).

4. The method of claim 1, wherein said π complex forming group is at least one selected from the group consisting of benzenesulfonyl, dinitrobenzenesulfonyl, benzoyl, dinitrobenzoyl and naphthoyl.

5. The method of claim 1, wherein said oligomer is selected from the group consisting of oligochitin and oligochitosan.

6. The method of claim 1, wherein said biocompatible oligomer comprises oligochitosan, said oligochitosan having an average molecular weight of less than 3,000 Da.

7. The method of claim 1, wherein a degree of substitution of said grafts is at least 20%.

8. The method of claim 1, wherein a degree of substitution of said grafts is at least 40%.

9. The method of claim 1, wherein said method provides a yield of said grafted oligomer of at least 40%.

10. A π-complex forming group functionalized biocompatible oligomer which has been produced by the method of claim 1.

11. The oligomer of claim 10, wherein said oligomer is selected from the group consisting of oligochitin and oligochitosan.

12. The oligomer of claim 10, wherein said oligomer comprises an oligochitosan, wherein a degree of substitution of said π complex forming group is at least 20%.

13. The oligomer of claim 10, wherein said π complex forming group is at least one selected from the group consisting of benzenesulfonyl, dinitrobenzenesulfonyl, benzoyl, dinitrobenzoyl and naphthoyl.

14. The oligomer of claim 10, wherein said biocompatible oligomer comprises oligochitosan, said oligochitosan having an average molecular weight of less than 3,000 Da.

15. The method of claim 1, wherein said π complex forming group is π-accepting.

16. The oligomer of claim 10, wherein said π complex forming group is π-accepting.

* * * * *